US00PP23124P2

(12) United States Plant Patent
Zaiger et al.

(10) Patent No.: US PP23,124 P2
(45) Date of Patent: Oct. 23, 2012

(54) INTERSPECIFIC ROOTSTOCK TREE NAMED 'NEWROOT-2'

(50) Latin Name: ***Interspecific Prunus* species**
Varietal Denomination: Newroot-2

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 13/506,676

(22) Filed: May 9, 2012

(51) Int. Cl.
*A01H 5/00* (2006.01)

(52) U.S. Cl. ..... Plt./180

(58) Field of Classification Search ..... Plt./180, Plt./185
See application file for complete search history.

*Primary Examiner* — June Hwu
*Assistant Examiner* — Louanne Krawczewicz Myers

(57) ABSTRACT

A new and distinct variety of interspecific rootstock tree grown on Handford sandy loam soil with Storie Index rating 95, in USDA Hardiness Zone 9, near Modesto, Calif., with standard commercial nursery practices. Its novelty consist of the following combination of desirable features in a new rootstock variety:

1. The ability to produce roots from dormant hardwood cuttings when planted directly in the field.
2. Well anchored root system.
3. Vigorous upright growth.
4. Has scion compatibility with plums, peaches and nectarines.
5. Rapid initiation of roots facilitates early spring budding in nursery.

1 Drawing Sheet

Botanical classification: Interspecific *Prunus* species.
Variety denomination: 'Newroot-2'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific rootstock tree was originated and asexually reproduced by us in our experimental orchard located near Modesto, Stanislaus County, Calif.

PRIOR VARIETIES

Among the existing varieties of rootstocks, cherry plum and flowering cherry, which are known to us, and mentioned herein, 'Newroot-1' Rootstock (U.S. Plant Pat. No. 21,723), 'Select Myroblan RI-1' Rootstock (U.S. Plant Pat. No. 14,126) and the proprietary seedling selections, '14G5' cherry plum (non-patented), '15G12' flowering cherry (non-patented).

STATEMENT REGARDING FEDERALLY SPONSORED RESEARCH AND DEVELOPMENT

Not applicable.

ORIGIN OF THE VARIETY

The new and distinct variety of interspecific tree, (*P. cerasifera*×*P. maximowiczii*) was originated by us in our experimental orchard located near Modesto, Calif. as a first generation cross between two proprietary seedling selections with the field identification numbers '14G5' cherry plum (non-patented) and '15G12' flowering cherry (non-patented). The seed parent '14G5' non-patented originated from seed of an open pollinated 'Myroblan' Plum Cherry (non-patented). The pollen parent originated from the flowering cherry selection '15G12' non-patented. A large number of these seedlings growing on their own root were evaluated for vigor and branch growth to determine the asexual reproduction of these seedlings from cuttings. One such seedling was selected for its desirable rooting ability and was tested by budding and grafting to various species and found to be very compatible with 'Select Myroblan RI-1' Rootstock (U.S. Plant Pat. No. 14,126) and was selected in 1994 for additional asexual propagation and commercialization.

ASEXUAL REPRODUCTION OF THE VARIETY

Asexual reproduction of the new and distinct variety of interspecific rootstock tree was by dormant rootstock cuttings, as performed by us in our experimental orchard located near Modesto, Calif., and shows that cutting reproductions run true to the original tree and all characteristics of the tree and its fruit are established and transmitted through succeeding asexual propagations.

SUMMARY OF THE NEW VARIETY

The new and distinct variety of interspecific rootstock tree (*Prunus cesasifera*×*Prunus maximowiczii*) is large in size, with upright growth, little or no suckering and the cuttings from this tree have the ability to develop roots when planted directly into the field. The present variety of interspecific rootstock is further characterized by rapid rooting of the cuttings allowing for early spring budding of the selections of peaches, nectarines, plums and 'Select Myrobalan RI-1'

(U.S. Plant Pat. No. 14,126). In comparison to its seed parent '14G5' (non-patented) the new variety does not produce root suckers and the fruit is larger in size. In comparison to its pollen parent '15G12' (non-patented) the new variety roots readily from hardwood cuttings and has larger, yellow-green fruit compared to small, red-black fruit. In comparison to 'Nemaguard' Rootstock (non-patented), which is propagated from seed, the new interspecific rootstocks grown from cuttings can be budded earlier in the nursery and at the end of the growing season the trees are approximately 20% larger in size. The trees budded and grown on the new interspecific rootstock produce larger size fruit which is approximately 2 to 4 days earlier in maturity than the same variety grown on 'Nemaguard' Rootstock (non-patented).

PHOTOGRAPH OF THE VARIETY

The accompanying color photographic illustration shows typical specimens of the foliage and fruit of the present new interspecific rootstock variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 14 year old tree and the colors are as nearly true as is reasonably possible in a color representation of this type.

DESCRIPTION OF THE VARIETY

The following is a detailed botanical description of the new variety of interspecific rootstock tree, its flowers, foliage and fruit, as based on observations of 14 year old specimens grown near Modesto, Calif., with color in accordance with Munsell Book of Color.

Tree:

*Size*.—Large, tree pruned severely each winter to induce proper new growth for rootstock cuttings. Average height 3.5 meters. Average width 3.0 meters, varies with different cultural practices.

*Vigor*.—Vigorous. Cut back to 1.5 meters each year to induce new growth for rootstock cuttings.

*Form*.—Upright.

*Branching habit*.—New growth from cut back branches have an approximate 45° angle. Branches grow approximately 1.0 to 1.5 meters each season to produce new wood for cuttings.

*Productivity*.—Productive, fruit has no commercial value.

*Bearer*.—Regular.

*Fertility*.—Self-sterile.

*Density*.—Dense, numerous branches develop from trees being cut back, this increases density.

*Hardiness*.—Tree grown in USDA Hardiness Zone 9. Hardy in all stone fruit growing areas of California.

Trunk:

*Size*.—Medium to large, circumference 46.9 cm measured at 31 cm above ground on a 14 year old tree.

*Stocky*.—Medium stocky.

*Texture*.—Medium shaggy, increases with age of tree.

*Color*.—Varies from 10YR 6/2 to 2.5Y 6/2.

Branches:

*Size*.—Medium, average circumference 10.3 cm at 1 meter above ground. Crotch angle approximately 45°, varies with tree branches being cut back each dormant season for additional cuttings.

*Surface texture*.—New growth relatively smooth. Mature growth medium rough. Roughness increases with age.

*Lenticels*.—Numerous — 63 in a 25.8 sq cm area. Average length 1.9 mm. Average width 0.7 mm. Color varies from 7.5YR 6/8 to 7.5YR 5/8.

*Color*.—New growth varies from 5GY 4/8 to 5YR 2/4. Old growth varies from 7.5YR 3/2 to 10YR 2/2, varies with age of growth.

Leaves:

*Size*.—Small to medium. Average length 77.8 mm. Average width 39.1 mm.

*Form*.—Elliptical.

*Apex*.—Acuminate.

*Base*.—Cuneate.

*Margin*.—Doubly serrate.

*Thickness*.—Medium.

*Surface texture*.—Upper surface relatively smooth, slightly indented over midrib and leaf veins, glabrous. Lower surface relatively smooth, small ridges created by midrib and pinnate venation, glabrous.

*Petiole*.—Average length 11.2 mm. Average width 1.3 mm. Color varies from 2.5GY 5/6 to 7.5R 2/4. Longitudinally grooved. Surface — very light pubescence.

*Glands*.—Eglandular.

*Stipules*.—Average length 7.7 mm. Edges — serrate. Color varies from 2.5GY 6/6 to 5GY 5/6.

*Color*.—Upper surface varies from 5GY 3/6 to 7.5GY 2/4. Lower surface varies from 5GY 4/4 to 7.5GY 4/4. Midvein color varies from 10Y 7/6 to 2.5GY 7/6.

Flower buds:

*Size*.—Small. Average length 8.7 mm. Average diameter 4.7 mm.

*Hardiness*.—Hardy in all stone fruit growing areas of California.

*Form*.—Plump, conical, becoming slightly elongated before opening.

*Pedicel*.—Average length 9.9 mm. Average width 0.7 mm. Color varies from 2.5GY 7/8 to 5GY 7/6.

*Color*.—N 9.5/ (white).

*Number of buds per spur*.—Average number 9, varies from 6 to 13.

Flowers:

*Blooming period*.—Date of First Bloom Feb. 28, 2011. Date of Petal Fall Mar. 9, 2011, varies slightly with climatic conditions.

*Size*.—Small to medium. Average height 10.7 mm. Average diameter 21.2 mm.

*Petals*.—Normally 5, alternately arranged to the sepals. Size — small to medium. Average length 10.3 mm. Average width 8.6 mm. Form — obovate, narrows at point of attachment. Margin — sinuate. Color — N 9.5/ (white).

*Sepals*.—Normally 5, alternately arranged to the petals. Size — small. Average length 3.4 mm. Average width 3.0 mm. Shape — ovate, somewhat triangular, tip rounded. Margin — entire. Both upper and lower surfaces glabrous. Color — upper surface varies from 5GY 6/10 to 5R 4/12. Lower surface varies from 5GY 6/8 to 5GY 6/10.

*Stamens*.—Average number per flower 33, varies from 32 to 34. Average filament length 8.9 mm. Filament color N 9.5/ (white). Anther color varies from 5Y 7/12 to 2.5Y 8.5/4.

*Pollen*.—Self-sterile. Color varies from 2.5Y 8/14 to 2.5Y 7/12.

*Pistil*.—Normally 1. Surface — glabrous. Average length 11.0 mm. Position of stigma even with anthers. Color varies from 2.5Y 8.5/14 to 5Y 8.5/8.

*Fragrance*.—Heavy aroma.

*Color*.—N 9.5/ (white).

*Number flowers per flower bud*.—Average 1, varies from 1 to 2.

*Pedicel*.—Average length 11.1 mm. Average width 0.7 mm. Color varies from 5GY 7/8 to 2.5GY 7/6.

Fruit:

*Maturity when described*.—Firm ripe, no commercial value.

*Date of fruit maturity*.—Jun. 20, 2011, varies slightly with climatic conditions.

*Size*.—Small to medium. Average diameter axially 48.9 mm. Average transversely in suture plane 44.8 mm. Average weight 59.6 grams, varies slightly with fertility of the soil and climatic conditions.

*Form*.—Globose.

*Suture*.—Nearly smooth, extends from base to apex.

*Ventral surface*.—Nearly smooth.

*Apex*.—Rounded.

*Base*.—Flat.

*Stem cavity*.—Rounded to slightly elongated in the suture plane. Average depth 2.0 mm. Average diameter 1.7 mm.

Stem:

*Size*.—Medium. Average length 14.2 mm. Average diameter 1.1 mm.

*Color*.—Varies from 2.5GY 6/8 to 2.5GY 5/6.

Flesh:

*Ripens*.—Evenly.

*Texture*.—Firm, meaty.

*Fibers*.—Few, small.

*Firmness*.—Firm.

*Aroma*.—Moderate.

*Amydgalin*.—Undetected.

*Eating quality*.—Poor, no commercial value.

*Flavor*.—Tart, acid.

*Juice*.—Moderate.

*Brix*.—Average 15.3°, varies slightly with amount of fruit per tree and climatic conditions.

*Color*.—Varies from 5Y 8/6 to 7.5Y 8/6.

*Pit cavity*.—Average length 24.0 mm. Average width 17.2 mm. Average depth 5.4 mm. Color 7.5Y 7/8.

Skin:

*Thickness*.—Medium.

*Surface*.—Smooth.

*Bloom*.—Moderate amount.

*Tendency to crack*.—Slight.

*Color*.—Ground color varies from 2.5GY 8/6 to 2.5GY 7/6. Overspread with 7.5Y 8/8 to 10Y 8.5/8.

*Tenacity*.—Tenacious to flesh.

*Astringency*.—Slight.

Stone:

*Type*.—Clingstone.

*Size*.—Medium. Average length 23.5 mm. Average width 16.1 mm. Average thickness 9.4 mm.

*Form*.—Ovoid.

*Base*.—Flat.

*Apex*.—Very slight point. Average length 0.9 mm.

*Surface*.—Very slightly pitted throughout.

*Sides*.—Unequal, one side extending further from the suture plane.

*Ridges*.—Very small ridge extends from base to apex.

*Tendency to split*.—None.

*Color*.—Varies from 10YR 7/6 to 10YR 6/8 when dry.

Kernel:

*Size*.—Medium. Average length 16.4 mm. Average width 10.7 mm. Average depth 6.0 mm.

*Form*.—Ovoid.

*Viability*.—Viable, complete embryo development.

*Skin color*.—Varies from 5Y 9/4 to 7.5Y 9/4.

Use: Rootstock.

Keeping quality: Not evaluated, fruit of no commercial value.

Shipping quality: Not evaluated, fruit of no commercial value.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific rootstock tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific rootstock tree, substantially as illustrated and described.

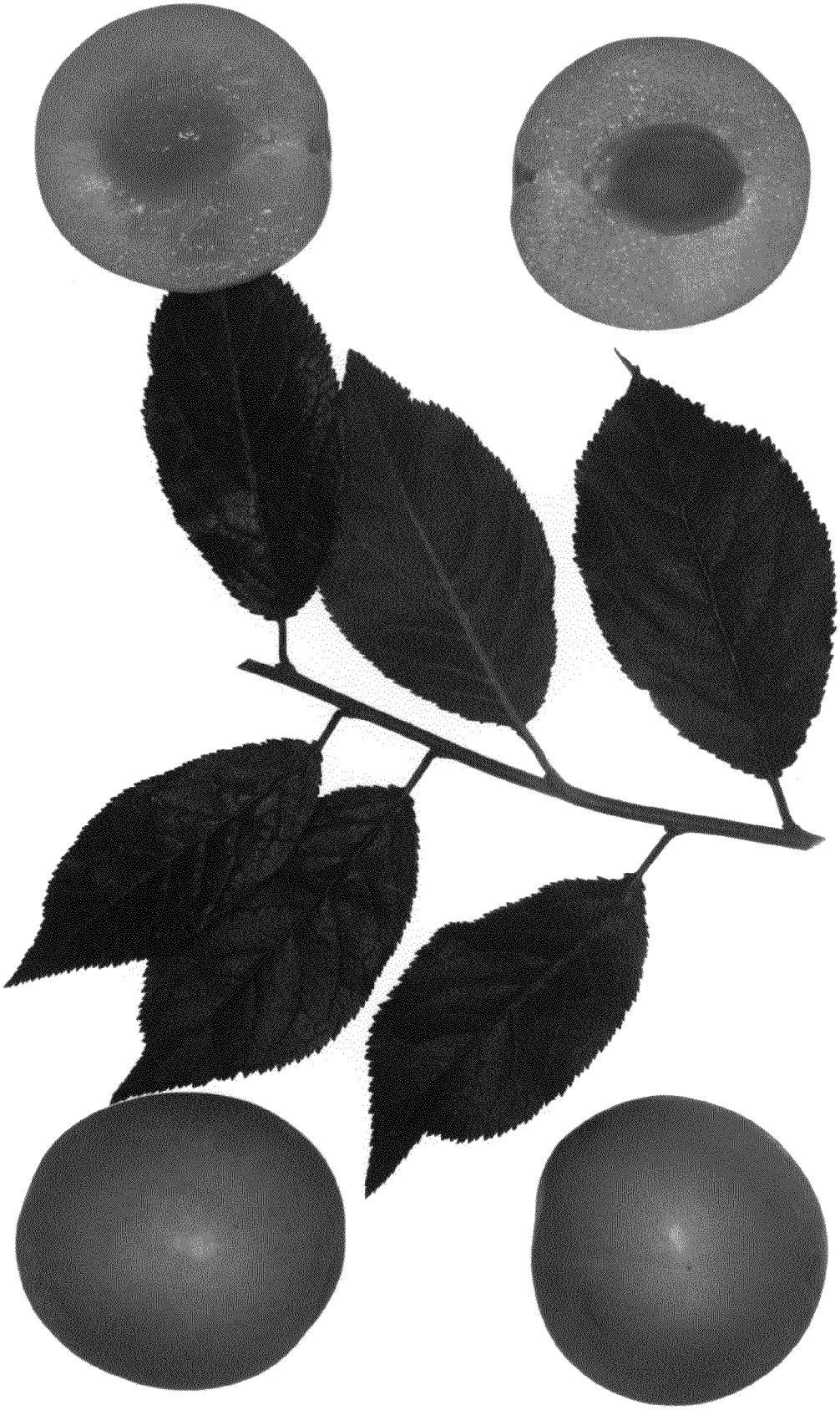

* * * * *